United States Patent [19]

Silver

[11] Patent Number: 4,604,092
[45] Date of Patent: Aug. 5, 1986

[54] LIQUID DRAINAGE SYSTEM WITH VERTICAL MOVABLE LIGHT EMITTER AND DETECTOR

[75] Inventor: Brian H. Silver, Skokie, Ill.

[73] Assignee: The Kendall Company, Boston, Mass.

[21] Appl. No.: 823,828

[22] Filed: Jan. 29, 1983

Related U.S. Application Data

[63] Continuation of Ser. No. 484,109, Apr. 11, 1983, abandoned.

[51] Int. Cl.⁴ .............................................. A61M 5/005
[52] U.S. Cl. .................................... 604/246; 604/260; 128/771; 73/293
[58] Field of Search ................ 604/246, 260, 317–318; 128/771; 73/293, 861

[56] References Cited

U.S. PATENT DOCUMENTS

| | | | |
|---|---|---|---|
| 2,948,186 | 8/1960 | Kendall | 73/293 |
| 3,511,572 | 5/1970 | Peube et al. | 73/293 |
| 4,014,010 | 3/1977 | Jinotti | 604/246 |
| 4,193,004 | 3/1980 | Lobdell et al. | 73/293 |
| 4,223,231 | 9/1980 | Sugiyama | 604/246 |
| 4,300,552 | 11/1981 | Cannon | 604/246 |
| 4,343,316 | 8/1982 | Jespersen . | |
| 4,383,252 | 5/1983 | Purcell et al. | 604/246 |
| 4,448,207 | 5/1984 | Parrish | 128/771 |

Primary Examiner—John D. Yasko
Assistant Examiner—Gene B. Kartchner
Attorney, Agent, or Firm—Powell L. Sprunger

[57] ABSTRACT

A liquid drainage system comprising, a container having a cavity to receive the liquid. The system has an associated light emitter and light detector being changeable between a first state with the light from the emitter impinging upon the detector, and a second state with the light from the emitter passing away from the detector dependent upon the presence of liquid in the container between the emitter and detector. The system has a device for moving the emitter and detector vertically along the container.

10 Claims, 3 Drawing Figures

LIQUID DRAINAGE SYSTEM WITH VERTICAL MOVABLE LIGHT EMITTER AND DETECTOR

This is a continuation of application Ser. No. 484,109, filed Apr. 11, 1983 now abandoned.

BACKGROUND OF THE INVENTION

The present invention relates to liquid drainage systems, and more particularly to devices such as urine drainage systems.

In the past, urine drainage systems have been known. Such systems normally comprise a container having a cavity to receive the urine, a catheter which is passed through the urethra of a patient until a distal end of the catheter is located in the patient's bladder, and a drainage tube communicating between a proximal end of the catheter located outside the patient's body and the container cavity. During use, urine drains from the bladder through the catheter and drainage tube into the container for collection therein.

The containers have normally been provided with a transparent wall with vertically disposed indicia on the wall. The volume of urine output was determined by comparing the level of urine in the container against the indicia. However, it is desirable to reduce the time of a nurse in using the system, and it also may be desirable to determine the flow rate of urine into the container.

SUMMARY OF THE INVENTION

A principal feature of the present invention is the provision of an improved liquid drainage system of simplified construction.

The drainage system of the present invention comprises, a container having a cavity to receive the liquid. The system has an associated light emitter and light detector with a vertical portion of the container being disposed between the emitter and detector. The system has means for moving the emitter and detector vertically along the container.

A feature of the present invention is that the emitter and detector are changeable between a first state with the light from the emitter impinging upon the detector when liquid is absent between the emitter and detector, and a second state with the light from the emitter being refracted away from the detector when the liquid is present between the emitter and detector.

Thus, a feature of the present invention is that the emitter and detector may be utilized to determine the height of liquid level in the container.

Another feature of the invention is that the emitter and detector may be moved vertically until the liquid level is ascertained in the container.

A further feature of the invention is that the determined liquid level may be utilized to ascertain the volume of liquid collected in the container.

Yet another feature of the invention is that the time of collection may be ascertained in order to determine the liquid flow rate into the container cavity.

Further features will become more fully apparent in the following description of the embodiments of this invention and from the appended claims.

DESCRIPTION OF THE PREFERRED EMBODIMENTS

Figure 1:
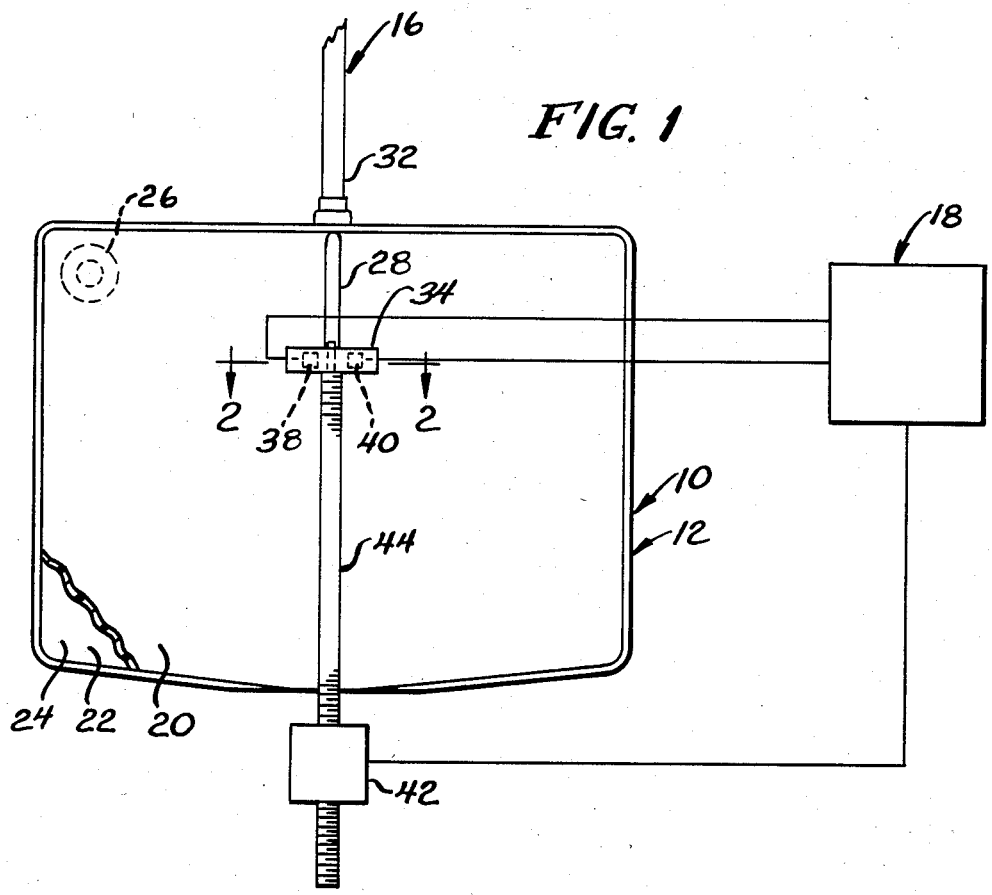
FIG. 1 is a fragmentary diagrammatic view of a liquid drainage system of the present invention.

Referring now to FIG. 1, there is shown a liquid drainage system 10 comprising a rigid container 12, a drainage tube 16 communicating with an upper portion of the container 12, and a central processing unit 18. The container 12 has a front wall 20 of rigid plastic material, and a back wall 22 of rigid plastic material, with the front wall 20 and back wall 22 being joined at their periphery in order to define a cavity 24 intermediate the front and back walls 20 and 22. The container 12 may have a vent 26 for the chamber 24, with the vent 26 having a bacteria filter of known type in order to filter bacteria from the air passing from the atmosphere into the cavity 24. The container 12 has a vertically extending protuberance 28 on the front wall 20, with the protuberance 28 defining a channel 30. A downstream end 32 of the tube 16 communicates with an upper portion of the cavity 24.

The system 10 has a housing 34 of transparent plastic material having a groove 36 to receive the protuberance 28, such that the housing 34 is slidably movable in a vertical direction along the protuberance 28. The housing 34 has a photoelectric light emitter 38 mounted in the housing 34 on one side of the protuberance 28, and a photoelectric light detector 40 mounted in the housing 34 on the other side of the protuberance 28. As shown, the emitter 38 is connected to the central processing unit 18 by an electrically conductive lead, and the emitter 38 is selectively energized by the central processing unit 18. Also, the detector 40 is connected by an electrically conductive lead to the central processing unit 18, such that the central processing unit 18 may detect a change of state in the detector 40.

The system 10 has a lower stepper motor 42 which is connected by one or more electrically conductive leads to the central processing unit 18 in order to energize the motor 42. The system 10 has a vertically disposed threaded rod or shaft 44 received in the motor 42, with an upper end of the shaft 44 being pivotally connected to the housing 34. The motor 42 has an internally threaded rotor which is fitted with the shaft 44. Energization of the motor coils by the central processing unit 18 in proper sequence will cause the threaded shaft 44 to move outwardly or back into the rotor in precise linear increments, such as 0.001 inch or 0.002 inch per pulse. As the motor 42 is energized and the shaft 44 moves in or out of the motor 42, the housing 34 and associated emitter 38 and detector 40 are caused to move vertically along the container 12.

Figure 2:
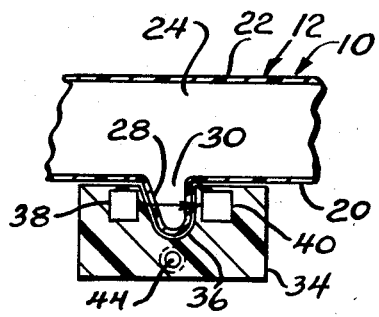
FIG. 2 is a fragmentary sectional view taken substantially as indicated along the line 2—2 of FIG. 1 illustrating use of a light emitter and light detector when liquid is absent between the emitter and detector.
Figure 3:
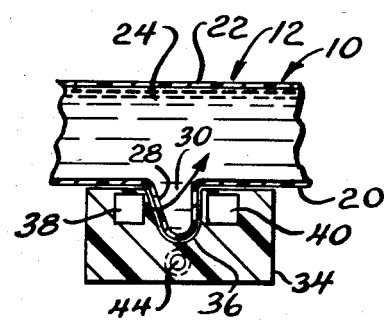
FIG. 3 is a sectional view similar to FIG. 2 illustrating use of the emitter and detector when liquid is present between the emitter and detector.

With reference to FIG. 2, when the liquid in the cavity 24 is absent between the emitter and detector 38 and 40, the emitter and detector 38 and 40 are in a first state with the light from the emitter 38 impinging upon the detector 40 which may be sensed by the central processing unit 18. With reference to FIG. 3, when the liquid level is present between the emitter 38 and detector 40 in a second state, the light from the emitter 38 is refracted by the liquid away from the detector 40 which may be sensed by the central processing unit 18. Of course, the container 12 and emitter and detector 38 and 40 may be designed such that light from the emitter 38 is refracted onto the detector 40 when liquid is present between the emitter and detector 38 and 40, and the light from the emitter 38 may pass away from the detector 40 when the liquid is absent between the emitter and detector 38 and 40.

In use of the system 10, the central processing unit 18 actuates the motor 42 to position the housing 34 at a predetermined lowermost position adjacent a lower portion of the cavity 24. The distal end of a catheter (not shown) is passed through the urethra of a patient until the distal end of the catheter is located in the patient's bladder, and an upstream end of the drainage tube 16 is connected to a proximal end of the catheter located outside the patient's body. Liquid drains through the catheter and drainage tube into the container cavity 24 for collection therein.

In accordance with the present invention, when it is desired to determine the volume of liquid collected in the container 12, the central processing unit 18 energizes the motor 42 in order to cause vertical movement of the shaft 44 and housing 34. Assuming a quantity of liquid has already been collected in the cavity 24, the emitter 38 and detector 40 will be in the second state, as shown in FIG. 3, when the housing 34 is located adjacent a lower portion of the container 12. When the housing 34 moves slightly above the liquid level in the cavity 24, the emitter 38 and detector 40 change to the first state, as shown in FIG. 2, and as sensed by the central processing unit 18, at which time the motor 42 may be stopped. The number of pulses applied to the motor 42 by the central processing unit 18 may be counted by the central processing unit 18 in order to reach the vertical position of the liquid level in the cavity 24. Each of the pulses applied to the motor 42 translates to a predetermined vertical movement of the housing 34 and associated emitter 38 and detector 40, and the vertical position of the liquid level in the cavity 24 may thus be calculated by the number of pulses applied to the motor 42 in order to position the housing 34 at the liquid level in the cavity 24. In turn, from the liquid level height in the cavity 24 the central processing unit 18 may calculate and display the volume of liquid in the container cavity 24 from the known dimensions of the container 12. Also, the central processing unit 18 may determine the time during collection of urine in the cavity 24 in order to calculate the liquid flow rate into the cavity 24 according to the volume of liquid in the cavity 24 and the time period of collection. The flow rate of the liquid into the cavity 24 may also be displayed by the central processing unit 18.

The foregoing detailed description is given for clearness of understanding only, and no unnecessary limitations should be understood therefrom, as modifications will be obvious to those skilled in the art.

I claim:

1. A liquid drainage system comprising:
   a container having a cavity to receive the liquid;
   an associated light emitter and light detector being changeable between a first state with the light from the emitter impinging upon the detector, and a second state with the light form the emitter passing away from the detector dependent upon the presence of liquid in the container between the emitter and detector; and
   means for moving the emitter and detector vertically along the container comprising means for housing the light emitter and light detector in fixed relationship to one another, a vertical threaded shaft arranged alongside the container, the housing means being mounted on top of the threaded shaft, and stepper motor means located beneath and in fixed relationship to the container, the vertical shaft being rotatable by the stepper motor means whereby upon energization of the stepper motor means, the housing and threaded shaft are caused to travel vertically alongside the container.

2. The system of claim 1 wherein said container includes a generally vertically extending protuberance defining a channel, with said emitter and detector being disposed on opposed sides of the protuberance and slidable along the protuberance.

3. The system of claim 1 including means for calculating the volume of liquid collected in the cavity.

4. The system of claim 1 including means for calculating the liquid flow rate into the cavity.

5. A liquid drainage system, comprising:
   a container having a cavity to receive the liquid;
   an associated light emitter and light detector with a generally vertical portion of the container being disposed between the emitter and detector, said emitter and detector being changeable between a first state with the light from the emitter impinging upon the detector when liquid is absent between the emitter and detector, and a second state with the light from the emitter being refracted away from the detector when the liquid is present between the emitter and detector; and
   means for moving the emitter and detector generally vertically along the container comprising means for housing the light emitter, and light detector in fixed relationship to one another, a vertical threaded shaft arranged alongside the container, the housing means being mounted on top of the threaded shaft, and stepper motor means located beneath and in fixed relationship to the container, the vertical shaft being threaded through and incrementally rotatable by the stepper motor means whereby upon energization of the motor means, the housing and threaded shaft are caused to travel vertically alongside the container.

6. The system of claim 5 wherein said container includes a generally vertically extending protuberance defining a channel, with said emitter and detector being disposed on opposed sides of the protuberance and slidable along the protuberance.

7. The system of claim 5 wherein the container is rigid.

8. The system of claim 5 wherein the housing is pivotally connected to the top of the threaded rod.

9. The system of claim 5 including means for calculating the volume of liquid collected in the cavity.

10. The system of claim 5 including means for calculating the liquid flow rate into the cavity.

* * * * *